United States Patent
Doan

(10) Patent No.: US 7,162,310 B2
(45) Date of Patent: Jan. 9, 2007

(54) FLAT WIRE HELIX ELECTRODE USED IN SCREW-IN CARDIAC STIMULATION LEADS

(75) Inventor: Phong D. Doan, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 105 days.

(21) Appl. No.: 10/842,888

(22) Filed: May 10, 2004

(65) Prior Publication Data

US 2005/0251240 A1    Nov. 10, 2005

(51) Int. Cl.
*A61N 1/05*    (2006.01)
(52) U.S. Cl. ..................................... 607/127
(58) Field of Classification Search ........ 607/126–128, 607/131; 600/375
See application file for complete search history.

(56) References Cited

U.S. PATENT DOCUMENTS

| 4,860,769 | A | | 8/1989 | Fogarty et al. | 128/786 |
|---|---|---|---|---|---|
| 4,920,979 | A | | 5/1990 | Bullara | 128/784 |
| 5,279,299 | A | * | 1/1994 | Imran | 600/393 |
| 5,354,327 | A | * | 10/1994 | Smits | 607/116 |
| 5,514,173 | A | * | 5/1996 | Rebell et al. | 607/127 |
| 5,545,201 | A | | 8/1996 | Helland et al. | 607/127 |
| 5,551,427 | A | | 9/1996 | Altman | 128/642 |
| 5,964,702 | A | | 10/1999 | Grill, Jr. et al. | 600/377 |
| 6,687,550 | B1 | | 2/2004 | Doan | 607/127 |

FOREIGN PATENT DOCUMENTS

| EP | 0042551 A1 | * | 12/1981 | 607/127 |
|---|---|---|---|---|
| EP | 0 092 797 B1 | | 11/1983 | |
| EP | 0 092 798 B1 | | 11/1983 | |
| EP | 0709111 A2 | | 5/1996 | |
| EP | 0709111 A3 | | 11/1997 | |

* cited by examiner

*Primary Examiner*—George R. Evanisko

(57) ABSTRACT

An implantable endocardial lead for use with a cardiac stimulation device includes an active fixation helix disposed at the distal end of the lead. The helix is constructed of flat wire having a non-circular cross section. The helix may be fixed or movable between a retracted position fully within the lead and an extended position advanced beyond the distal end of the lead.

12 Claims, 4 Drawing Sheets

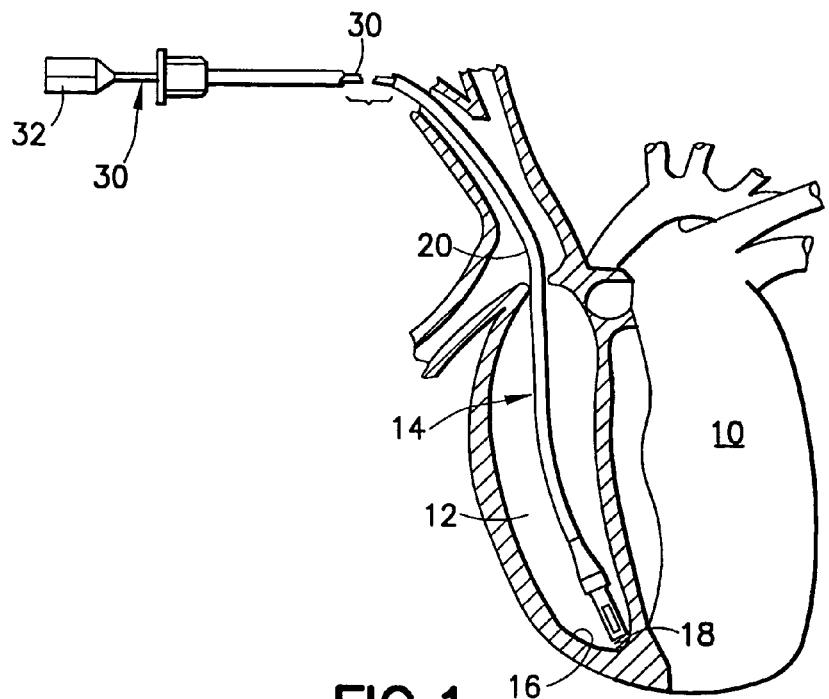
FIG. 1
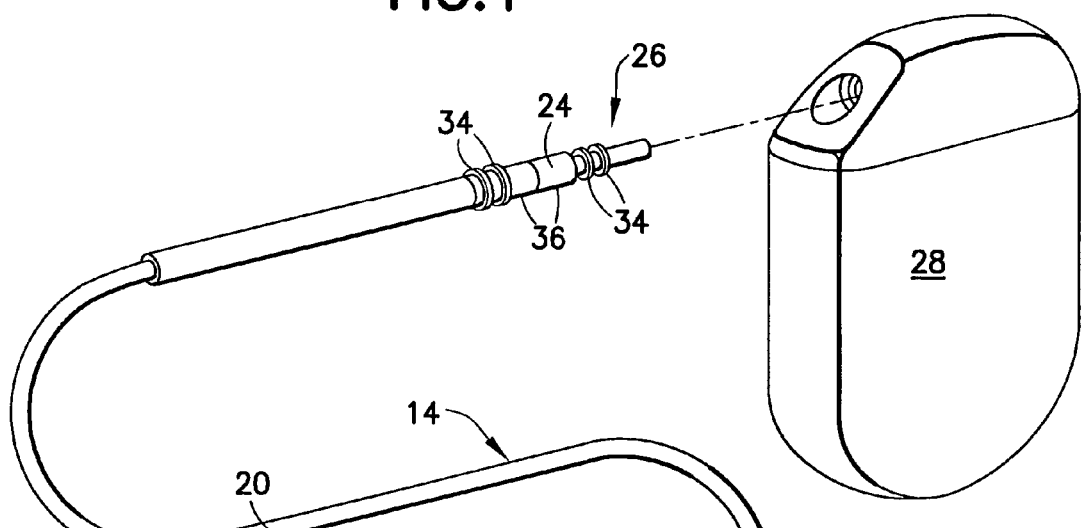
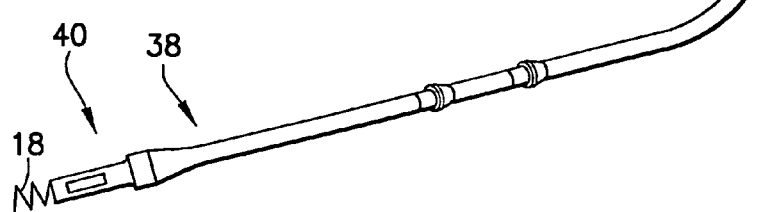
FIG. 2

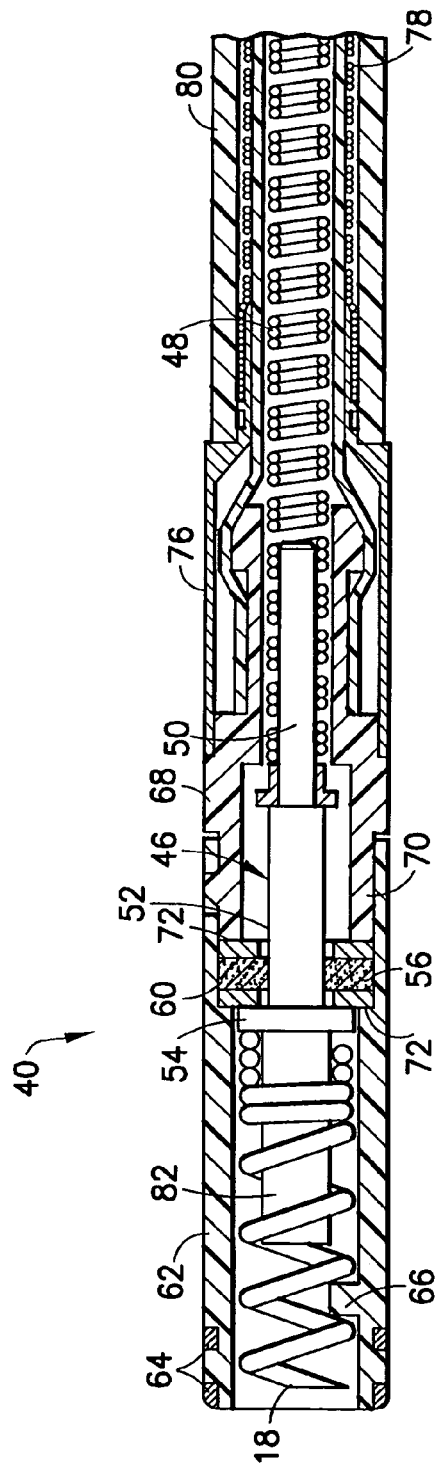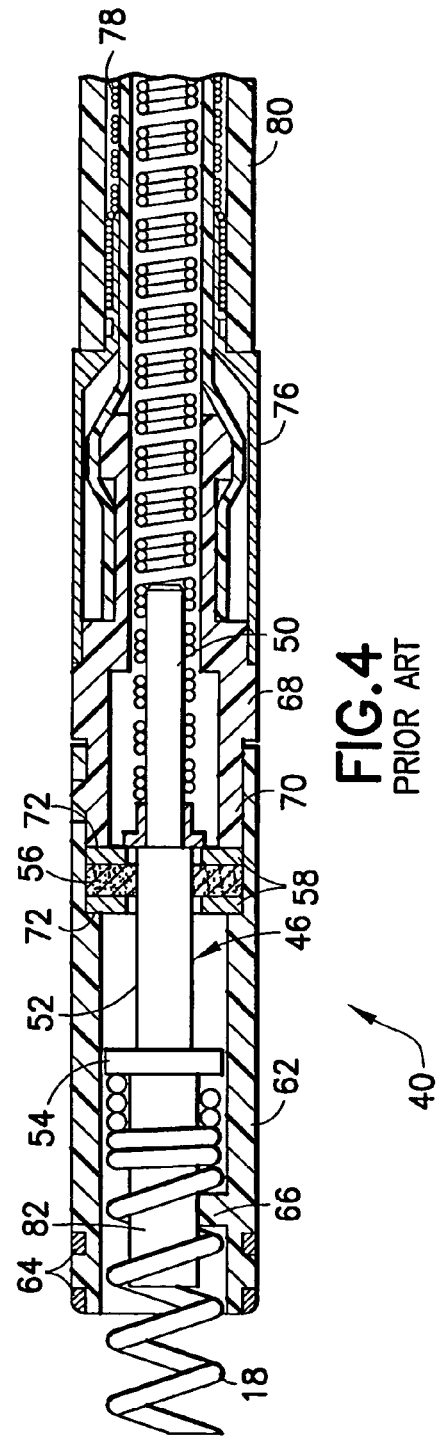
FIG. 3 PRIOR ART
FIG. 4 PRIOR ART

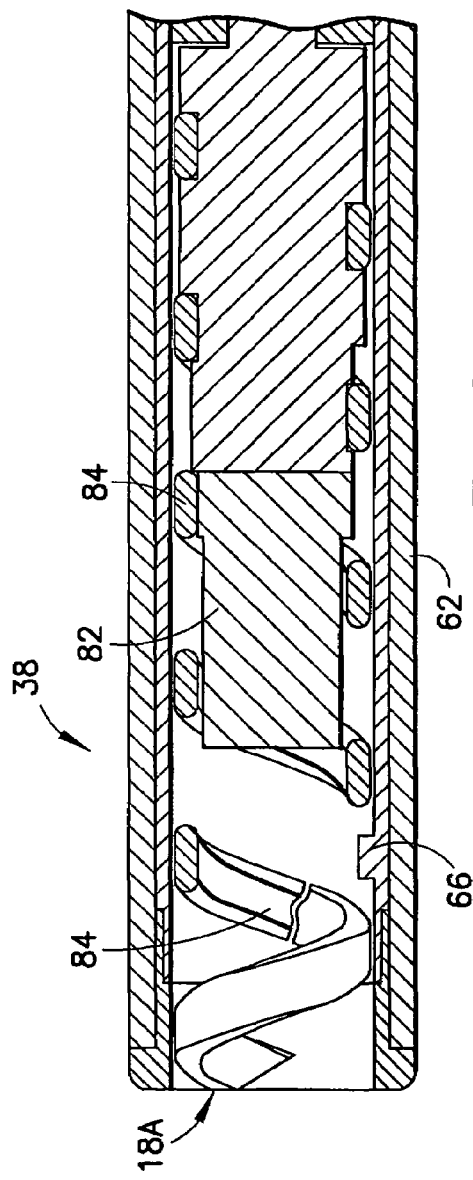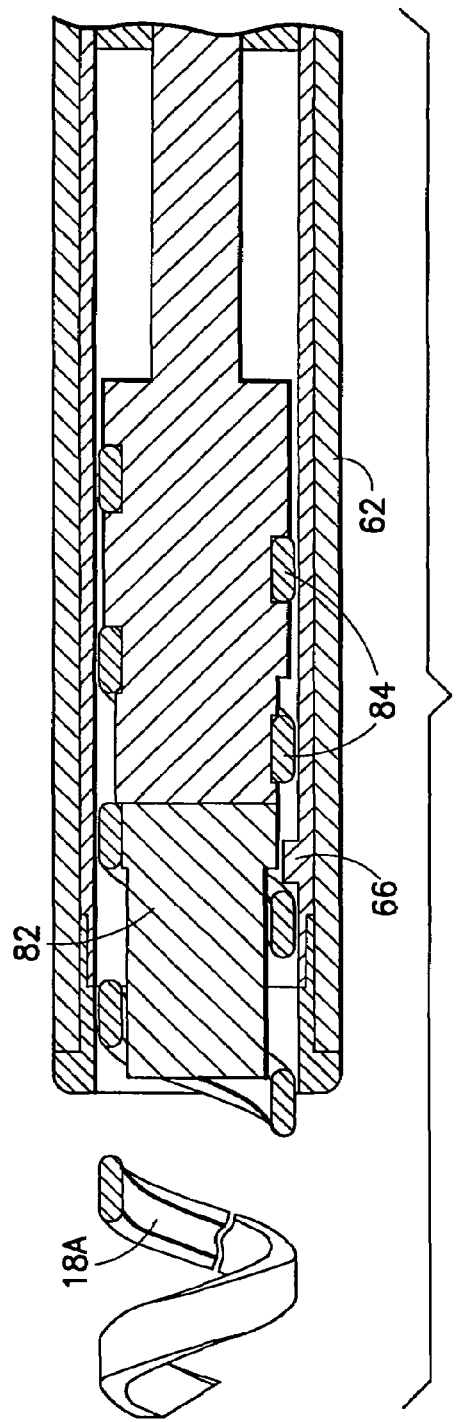

FLAT WIRE HELIX ELECTRODE USED IN SCREW-IN CARDIAC STIMULATION LEADS

FIELD OF THE INVENTION

The present invention relates generally to implantable stimulation leads for use with an implantable pulse generator such as a cardiac pacemaker or defibrillator and, more specifically, to such an implantable stimulation lead with the capability of selectively anchoring an electrically active helix electrode of improved design at a desired site when the lead is fixated in the heart.

BACKGROUND

Currently, known extendable/retractable screw-in implantable stimulation leads have an electrically active helix electrode. The helix electrode may be capable of extension and retraction from the header by being directly connected to the connector pin/distal coil subassembly. Turning of the connector pin results in the extension or retraction of the helix electrode from the header. In order for the helix to be extended or retracted, a thread/screw mechanism is required. The helix electrode is used as a threaded screw which turns against a thread post in the header. As the helix rotates, by turning of the connector pin, it engages the thread post, which in turn drives the helix into and out of the header.

Leads are also known which employ a fixed extended electrically active helix electrode and the invention is applicable to such leads as well.

Traditionally, the helix electrode of either fixed screw-in or extendable and retractable screw-in leads is made out of a round wire. The size of the wire should be small enough so as not to severely damage the heart tissue but thick enough to achieve good fixation while being visible under fluoroscopy. In addition, the outer diameter of the helix electrode should be sufficiently large to achieve a good and less traumatic fixation but not too small to core out the heart tissue. Currently, the appropriate range of the helix wire diameter is between about 10 mils (0.010 inches) and 13 mils (0.013 inches) and the outer diameter of the helix wire desirably ranges from about 0.040 inches to 0.070 inches. The outer diameter of the helix and the helix wire diameter must be balanced in order to create a first class helix electrode. In order to downsize the distal tip of a screw-in lead for a smaller lead, besides other design considerations at the distal tip, the helix wire size and outer diameter could be reduced to a certain extent. However, further reduction of the helix wire size or helix outer diameter would compromise the performance of the helix electrode in terms of electrode pacing threshold and helix visibility. The invention allows for more design options for the tip of a smaller lead without compromising helix performance.

Typical of the known prior art is U.S. Pat. No. 4,860,769 to Fogarty et al. which provides for an implantable defibrillator electrode including a flexible insulated guide terminating in a flexible distal portion which includes a conductive element and is of a predetermined configuration, such that it may be extended to a linear configuration by the application of a concentric or axial force and upon the termination of such force assumes the predetermined configuration. The conductive portion of the electrode may be a spiral of flat wire helically wound on a generally cylindrical, non-conductive stem.

Another example of the prior art can be found in U.S. Pat. No. 4,920,979 to Bullara which discloses a circumneural electrode assembly including a supportive flexible and insulating matrix formed into two oppositely directed helical portions which are centrally joined, and have free outer ends. The helical portions extend circumferentially at least one full turn, and preferably about one-half additional turn, for a total extent in the range of 360 degrees to 720 degrees. A thin and flexible conductive ribbon, preferably of surface-roughened platinum, is secured to the inner surface of one of the helical portions, and multiple electrodes can be provided on one or both portions. A connecting wire or cable extends from the electrode and matrix for coupling to an electronic package which is normally implanted elsewhere in the patient's body.

Still another example of the prior art can be found in U.S. Pat. No. 5,964,702 to Grill, Jr. et al. which discloses a helical nerve cuff electrode which is provided for encircling a nerve trunk or other body tissue with at least one medication or electrically energy conductive member disposed along the length of the helical cuff. The cuff includes a self-curling sheet of non-conductive material laminations which are collectively self-biased to curl into a tight helix.

SUMMARY

An implantable endocardial lead for use with a cardiac stimulation device includes an internal electrical conductor and an active fixation electrode with a coaxial electrically active helix coupled to the distal end of the electrical conductor for effecting penetration into the myocardial tissue. The electrode is constructed of flat wire having a non-circular, such as quadrilateral or elliptical, cross section. The electrically active helix may be fixed or movable between a retracted position fully within the lead and an extended position advanced beyond the distal end of the lead. An insulation sheath of silicone or polyurethane covers the electrical conductor defining an internal chamber extending from the proximal end to the distal end and an electrical connector is coupled to the proximal end of the electrical conductor. With this construction, the outer diameter of the electrode is in the range of about 3 French (0.039 inches) to 9 French (0.118 inches) and the cross sectional dimension of the electrode wire is greater in the direction of the longitudinal axis of the lead than in a direction transverse of the longitudinal axis of the lead, being in the range of about 0.002 inches×0.008 inches to about 0.005 inches×0.015 inches.

Thus instead of using round wire, flat wire with a thickness typically thinner than the diameter of the round wire, is used for the helix electrode. It could be used for smaller diameter helix electrodes while maintaining other critical design parameters and potentially increasing fluoroscopic visibility of the helix due to a wider profile of the flat wire as compared with the round, conventional, wire.

Other and further features, advantages, and benefits will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the illustrative embodiment in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein:

FIG. 1 is a perspective view illustrating a heart with a portion cut away to reveal an implantable lead assembly according to one illustrative embodiment and secured therein to a wall of the heart;

FIG. 2 is a perspective view of an implantable lead in combination with a cardiac stimulation device such as a pacemaker or defibrillator;

FIG. 3 is a longitudinal cross section view of a known electrode assembly at the distal end of the type of lead illustrated in FIG. 1, with the helical electrode in the retracted position;

FIG. 4 is a longitudinal cross section view of the known electrode assembly at the distal end of the pacing lead with the helical electrode in the extended position;

FIG. 6 is a cross section view taken generally along line 6—6 in FIG. 5;

FIG. 7 is a cross sectional view, similar to FIG. 6, illustrating the helical flat wire electrode in the extended position;

DETAILED DESCRIPTION OF THE PREFERRED EMBODIMENT

Figure 5:
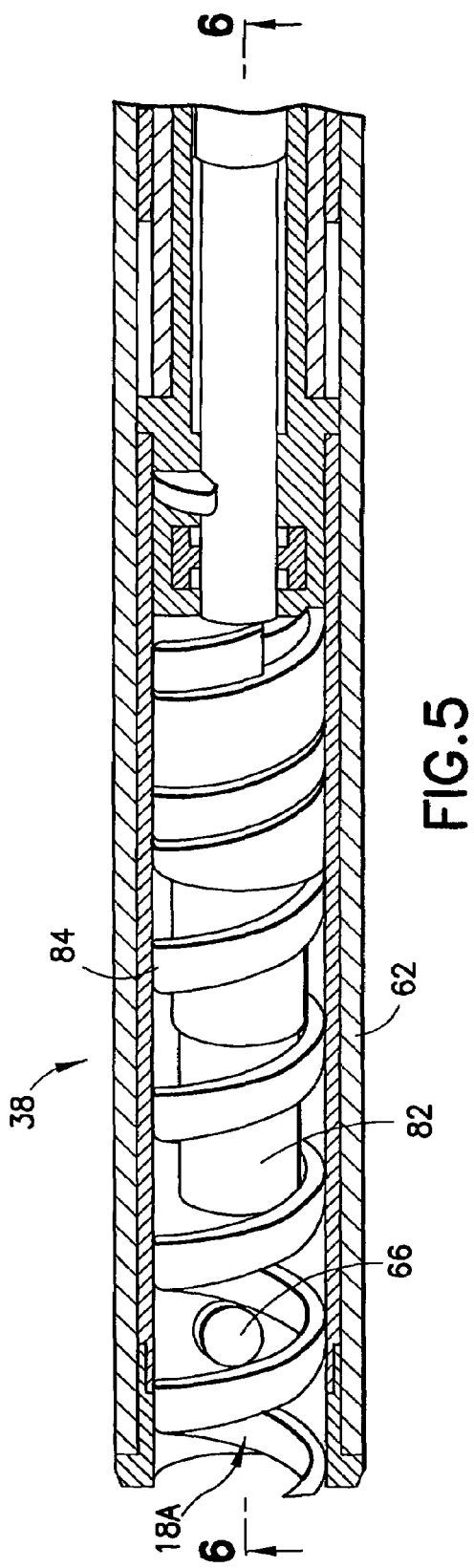
FIG. 5 is a detail perspective view of the distal end of the lead illustrated in FIG. 1, with the helical flat wire electrode in the retracted position.

Referring to FIG. 1, there is shown a diagrammatic perspective view partially cut away and shown in section of a heart 10 into the right ventricle 12 of which is inserted a body implantable lead 14 of the endocardial type according to one illustrative embodiment. Although certain illustrative embodiments are shown in the drawings, it should be understood that the present invention can be embodied in many alternate forms or embodiments. In addition, any suitable size, shape or type of elements or materials could be used. The lead 14 of an active fixation design is attached to an interior wall 16 of the heart 10 by means of a fixing helix 18 which engages the tissue or trabeculae of the heart.

As further illustrated, the lead 14 also includes an insulation sheath 20 interconnecting the helix 18 secured to the interior wall 16 and an electrical connector 24 at a proximal end 26 to which can be attached a cardiac stimulation device 28 such as a pacemaker or defibrillator (FIG. 2). In FIG. 1, a stylet 30 is illustrated inserted within the insulation sheath 20 and may be used to provide rigidity to the lead 14 during insertion of the lead into the heart 10. The elongated stylet 30 extends through a lumen of the insulation sheath 20 between a distal attachment device and a proximal manipulating device 32. The manipulating device is distant from the distal attachment device and may be a finger grip at a proximal extremity of the stylet 30 provided for controlling the introduction of the stylet into the lead 14 and its subsequent withdrawal.

The lead 14 is designed for intravenous insertion and contact with the endocardium and, as such, may be conventionally referred to as an endocardial lead. The lead 14 includes coil or helically wound electrical conductors (not shown in this view) covered with the insulation sheath 20. The insulation sheath is preferably fabricated of silicone rubber, polyurethane or other suitable plastic material. At the proximal end 26 of the lead 14, the connector assembly 24 is provided with sealing rings 34 and carries at least one, and preferably a pair, of electrical contacts 36.

The connector assembly 24 is constructed using known techniques and is preferably fabricated of silicone rubber, polyurethane or other suitable plastic material. Contacts 32 are preferably fabricated of stainless steel or other suitable electrically conductive material. The lead 20 is constructed to include a hollow interior extending from the proximal end 26 to a distal end 38. As earlier mentioned, the hollow interior of the lead 14 allows for the introduction of a stylet during implant, which is beneficial in allowing the surgeon to guide the otherwise flexible lead from the point of venous insertion to the myocardium.

At the distal end 38 of the lead 14 is an electrode assembly 40 which may take many different forms. For example, lead 14 may include one or more ring electrodes for bipolar sensing and pacing, as is well known in the art. Lead 14 may further include a defibrillation electrode for delivering defibrillation shocks. In these embodiments, one or more conductors extend through the lead housing to conduct electrical energy to the various electrodes. Furthermore, in at least one embodiment, the helix fixation member 18 may be electrically inactive, with the sensing and pacing functions being performed by the electrode assembly 40.

FIGS. 3 and 4 depict a known construction for the distal end 38 of the lead 14 of FIG. 1. In FIGS. 3 and 4 the helix or helical electrode 18 is seen affixed to an advanceable electrical interconnect 46. The electrical interconnect 46 is also electrically connected to the conductor 48 which extends from the distal end to the proximal end of the lead 14. The electrical interconnect 46 thus includes a tail portion 50, to which the conductor 48 is secured, a central shaft portion 52 and a head portion 54. The helical electrode 18 is connected to the head portion 54. The central shaft portion 52 of the electrical interconnect 46 passes through a seal assembly 56. The seal assembly 56 may include a pair of retaining rings 58 which cooperate to secure a resilient ring seal 60. The seal assembly 56 prevents bodily fluids from penetrating into the axial void extending through the center of the lead 14.

As also depicted in FIGS. 3 and 4, the distal end 38 of the lead 14 terminates in a sleeve 62 which is essentially a cylindrical element having a central bore within which the helical electrode 18 is disposed and retractable. The sleeve 62 is preferably fabricated from a biocompatible elastomeric material. The distal tip of sleeve 62 may include one or more metallic rings 64, which are useful during implant to allow a physician to verify the position of the helical electrode 18 relative to the metallic ring 64 in either the extended or retracted position by the use of a fluoroscope. Further, the sleeve 62 includes a knob 66 extending from the inner diameter to guide the rotative advancement of the helical electrode 18. It is to be understood that techniques for implanting a pacing lead and advancing the fixation elements are known in the art, and, therefore, will not be discussed here.

The proximal end of the sleeve 62 is affixed to a stepped cylindrical element 68, which is preferably formed from a biocompatible nonconductive material. The stepped cylindrical element 68 includes a cylindrical portion 70 which slides into the proximal end of the cylindrical sleeve 62 and is bonded thereto. The seal assembly 56 is located between an end-face 72 of the stepped cylindrical element 68 and an internal step 74 of the sleeve 62.

As further illustrated in FIGS. 3 and 4, the proximal end of the distal assembly 36 may include a second ring electrode or sensor electrode 76 spaced proximally of the distal tip. The ring electrode 76 is electrically interconnected to a second conductor 78 which also extends from the proximal to the distal end of the lead body 22 and is helically wrapped about the cylindrical insulation containing the first conductor 48. The second electrical conductor 78 is also preferably encased in an insulation sleeve 80. The second electrical conductor 78 extends to and interconnects with an electrical contact (not shown) located at the connector assembly 28 at the proximal end 26 of the lead 14.

In FIGS. 3 and 4, a therapeutic delivery means is provided which includes a therapeutic bullet 82 centrally disposed with respect to the helical electrode 18, that is, along the axis of the helix. The therapeutic bullet 82 is preferably secured to the head portion 54 of the electrical interconnect 46, and advanceable therewith. As depicted in FIG. 4, when the helical electrode 18 is fully extended and inserted into the myocardium upon implant, the therapeutic bullet 82 does not extend out of the end of the sleeve 62 as does the helical electrode 18. Although, according to the design illustrated in FIGS. 3 and 4, the therapeutic bullet 82 is only advanceable with the advancement of the electrical interconnect 46, other constructions are known according to which the therapeutic bullet is independently advanceable.

Turn now to FIGS. 5–9, which show illustrative embodiments of a lead. The distal end 38 of the lead 14 is clearly seen in FIGS. 5–7. FIGS. 5 and 6 illustrate a modified electrically active helical electrode 18A in its retracted position and FIG. 7 illustrates the electrode 18A in its extended position. In this instance, the electrode 18A is constructed of flat wire having a non-circular cross section and, more specifically, is constructed of flat wire 84 having a quadrilateral cross section. This cross section of the electrode 18A is most clearly seen in FIG. 8 and it will be appreciated that the cross sectional dimension of the electrode wire is greater in the direction of the longitudinal axis of the lead 14 than in a direction transverse of that longitudinal axis. The outer diameter of the electrode 18A is in a distinctly superior range of about 3 Fr to 9 Fr. Because of the wider profile of the flat wire, its visibility under fluoroscopy is much improved over electrodes using wire of round cross section. Additionally, when such an electrode is used, distinct edges 86 of the flat wire 84 provide an improved pacing threshold due to edging effect. For the electrode 18A, preferred cross sectional dimensions of the electrode wire 84 are in the range of 0.002 inches×0.008 inches to about 0.005 inches×0.015 inches.

Figure 9:
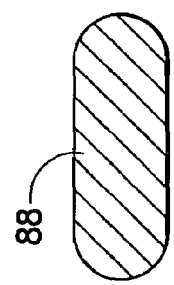
FIG. 9 is a cross section view of a helical electrode wire according to one illustrative embodiment having an elliptical cross section.
Figure 8:
FIG. 8 is a cross section view of a helical electrode wire according to one illustrative embodiment having a quadrilateral cross section.

In another instance, viewing FIG. 9, a further modified electrode may be constructed of flat wire 88 having an elliptical cross section.

It should be understood that the foregoing description merely describes illustrative embodiments of leads. Various alternatives and modifications can be devised by those skilled in the art without departing from the invention. Accordingly, the invention should be determined by reference to the appended claims.

What is claimed is:

1. An implantable endocardial lead having a longitudinal axis and extending between proximal and distal ends, the implantable endocardial lead being for use with a cardiac stimulation device and comprising:
   an electrical conductor within the lead extending between proximal and distal ends; and
   an active fixation electrode comprising an electrically active helix coupled to the distal end of the electrical conductor, the electrode being constructed of flat wire having a non-circular cross section;
   wherein the cross sectional dimension of the electrode wire is greater in the direction of the longitudinal axis of the lead than in a direction transverse of the longitudinal axis of the lead; and
   wherein the cross sectional dimension of the electrode wire is in the range of about 0.002 inches×0.008 inches to about 0.005 inches×0.015 inches.

2. An implantable endocardial lead as set forth in claim 1 wherein the electrode is constructed of flat wire having a quadrilateral cross section.

3. An implantable endocardial lead as set forth in claim 1 wherein the electrode is constructed of flat wire having a partially elliptical cross section.

4. An implantable endocardial lead as set forth in claim 1 wherein the electrically active helix is movable between a retracted position fully within the lead and an extended position advanced beyond the distal end of the lead.

5. An implantable endocardial lead as set forth in claim 1 including:
   an insulation sheath covering the electrical conductor defining an internal chamber extending from the proximal end to the distal end; and
   an electrical connector being coupled to the proximal end of the electrical conductor.

6. An implantable endocardial lead as set forth in claim 5 wherein the insulation sheath is composed of at least one of silicone and polyurethane.

7. An implantable endocardial lead as set forth in claim 1 wherein the outer diameter of the electrode is in the range of about 3 fr to 9 fr.

8. An implantable endocardial lead comprising:
   a lead body;
   an electrical conductor extending within the lead body;
   at least one electrode mounted on the lead body and connected to the electrical conductor; and
   an active fixation helix disposed at the distal end of the lead body, the active fixation helix being constructed of flat wire having a non-circular cross section;
   wherein the cross sectional dimension of the flat wire is greater in the direction of the longitudinal axis of the lead than in a direction transverse of the longitudinal axis of the lead; and
   wherein the cross sectional dimension of the flat wire is in the range of about 0.002 inches×0.008 inches to about 0.005 inches×0.015 inches.

9. The implantable endocardial lead of claim 8 and further comprising
   an electrical conductor connected to the active fixation helix, wherein the active fixation helix is electrically active.

10. The implantable endocardial lead as set forth in claim 8 wherein the active fixation helix is constructed of flat wire having a quadrilateral cross section.

11. The implantable endocardial lead as set forth in claim 8 wherein the active fixation helix is constructed of flat wire having a partially elliptical cross section.

12. The implantable endocardial lead as set forth in claim 8 wherein the active fixation helix is movable between a retracted position fully within the lead and an extended position advanced beyond the distal end of the lead.

* * * * *